US011410766B2

(12) United States Patent
Schreier et al.

(10) Patent No.: US 11,410,766 B2
(45) Date of Patent: Aug. 9, 2022

(54) METHODS AND SYSTEMS FOR RADIOTHERAPY TREATMENT PLANNING BASED ON CONTINUOUS DEEP LEARNING

(71) Applicant: Varian Medical Systems International AG, Palo Alto, CA (US)

(72) Inventors: Jan Schreier, Helsinki (FI); Hannu Laaksonen, Espoo (FI); Heini Hyvonen, Helsinki (FI)

(73) Assignee: VARIAN MEDICAL SYSTEMS INTERNATIONAL AG

(*) Notice: Subject to any disclaimer, the term of this patent is extended or adjusted under 35 U.S.C. 154(b) by 146 days.

(21) Appl. No.: 16/432,943

(22) Filed: Jun. 6, 2019

(65) Prior Publication Data

US 2020/0388371 A1 Dec. 10, 2020

(51) Int. Cl.
*G16H 20/40* (2018.01)
*G16H 50/20* (2018.01)
*G16H 30/40* (2018.01)

(52) U.S. Cl.
CPC ............ *G16H 20/40* (2018.01); *G16H 30/40* (2018.01); *G16H 50/20* (2018.01)

(58) Field of Classification Search
CPC ........ G16H 30/40; G16H 20/40; G16H 30/20; G16H 50/70; G16H 70/20; G16H 20/00;
(Continued)

(56) References Cited

U.S. PATENT DOCUMENTS

2016/0140300 A1* 5/2016 Purdie .................. G16H 10/60
705/2
2018/0161596 A1 6/2018 Kuusela et al.
(Continued)

FOREIGN PATENT DOCUMENTS

EP 3576100 A1 * 12/2019 ............. G16H 50/20
WO 2019027924 A1 2/2019

OTHER PUBLICATIONS

Chen, Xinyuan, et al. "A feasibility study on an automated method to generate patient-specific dose distributions for radiotherapy using deep learning." Medical physics 46.1 (2018): 56-64. (Year: 2018).*
(Continued)

*Primary Examiner* — Jason B Dunham
*Assistant Examiner* — Constantine B Siozopoulos
(74) *Attorney, Agent, or Firm* — Su IP Consulting (57) ABSTRACT

Example methods and systems for radiotherapy treatment planning based on continuous deep learning are provided. One example method may comprise: obtaining a deep learning engine that is trained to perform a radiotherapy treatment planning task based on first training data associated with a first planning rule. The method may also comprise: based on input data associated with a particular patient, performing the radiotherapy treatment planning task using the deep learning engine to generate output data associated with the particular patient; and obtaining modified output data that includes one or more modifications to the output data generated by the deep learning engine. The method may further comprise: based on the modified output data, generating second training data associated with a second planning rule; and generating a modified deep learning engine by re-training the deep learning engine using a combination of the first training data and the second training data.

21 Claims, 8 Drawing Sheets

(58) Field of Classification Search
CPC ............ G06T 2207/10088; G06T 7/11; G06N 3/0454; G06N 20/00; G06N 5/025
See application file for complete search history.

(56) References Cited

U.S. PATENT DOCUMENTS

| | | |
|---|---|---|
| 2018/0315188 A1 | 11/2018 | Tegzes et al. |
| 2019/0051398 A1 | 2/2019 | Zankowski et al. |
| 2019/0251694 A1* | 8/2019 | Han .......................... G06T 7/11 |
| 2019/0333623 A1* | 10/2019 | Hibbard ................. G16H 20/40 |

OTHER PUBLICATIONS

International Search Report and Written Opinion of the International Searching Authority, International application No. PCT/EP2020/065541, dated Aug. 13, 2020.

* cited by examiner

METHODS AND SYSTEMS FOR RADIOTHERAPY TREATMENT PLANNING BASED ON CONTINUOUS DEEP LEARNING

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, to achieve this goal, conventional radiotherapy treatment planning may be time and labor intensive.

SUMMARY

According to examples of the present disclosure, methods and systems for radiotherapy treatment planning based on continuous deep learning are provided. In this case, one example method may comprise: obtaining a deep learning engine that is trained to perform a radiotherapy treatment planning task based on first training data associated with a first planning rule. The method may also comprise: based on input data associated with a particular patient, performing the radiotherapy treatment planning task using the deep learning engine to generate output data associated with the particular patient; and obtaining modified output data that includes one or more modifications to the output data generated by the deep learning engine. The method may further comprise: based on the modified output data, generating second training data associated with a second planning rule; and generating a modified deep learning engine by re-training the deep learning engine using a combination of the first training data and the second training data.

DETAILED DESCRIPTION

The technical details set forth in the following description enable a person skilled in the art to implement one or more embodiments of the present disclosure.

Figure 1:
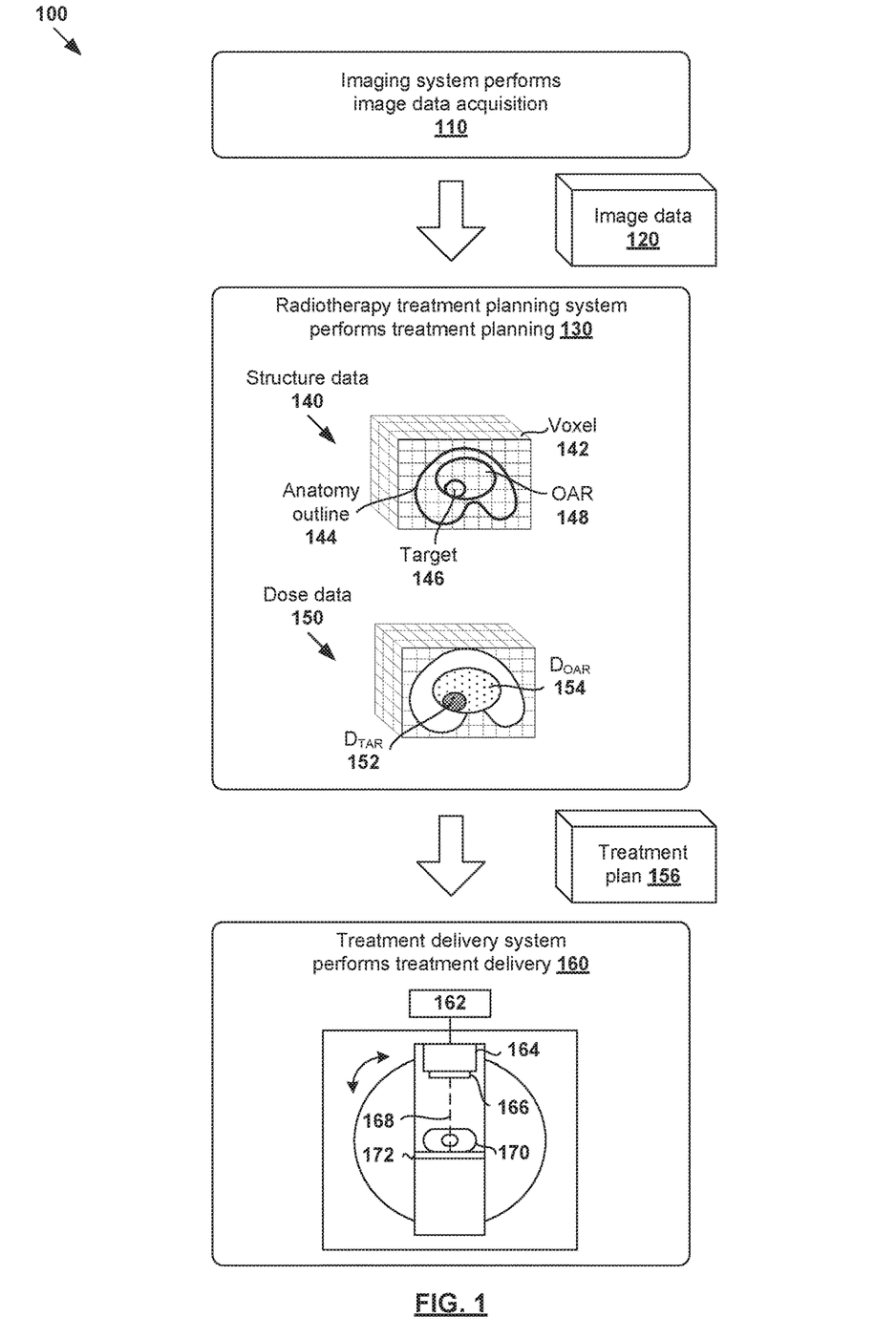
FIG. 1 is a schematic diagram illustrating an example process flow for radiotherapy treatment.

FIG. 1 is a schematic diagram illustrating example process flow 100 for radiotherapy treatment. Example process 100 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 156) for the patient; and a treatment delivery system (see 160) delivering treatment according to the treatment plan.

In more detail, at 110 in FIG. 1, image data acquisition may be performed using an imaging system to capture image data 120 associated with a patient (particularly the patient's anatomy). Any suitable medical image modality or modalities may be used, such as computed tomography (CT), cone beam computed tomography (CBCT), positron emission tomography (PET), magnetic resonance imaging (MRI), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or 4D CBCT).

At 130 in FIG. 1, radiotherapy treatment planning may be performed during a planning phase to generate treatment plan 156 based on image data 120. Any suitable number of treatment planning tasks or steps may be performed, such as segmentation, dose prediction, projection data prediction, treatment plan generation, etc. For example, segmentation may be performed to generate structure data 140 identifying various segments or structures from image data 120. In practice, a three-dimensional (3D) volume of the patient's anatomy may be reconstructed from image data 120. The 3D volume that will be subjected to radiation is known as a treatment or irradiated volume that may be divided into multiple smaller volume-pixels (voxels) 142. Each voxel 142 represents a 3D element associated with location (i, j, k) within the treatment volume. Structure data 140 may be include any suitable data relating to the contour, shape, size and location of patient's anatomy 144, target 146, organ-at-risk (OAR) 148, or any other structure of interest (e.g., tissue, bone). For example, using image segmentation, a line may be drawn around a section of an image and labelled as target 146 (e.g., tagged with label="prostate"). Everything inside the line would be deemed as target 146, while everything outside would not.

In another example, dose prediction may be performed to generate dose data 150 specifying radiation dose to be delivered to target 146 (denoted "$D_{TAR}$" at 152) and radiation dose for OAR 148 (denoted "$D_{OAR}$" at 154). In practice, target 146 may represent a malignant tumor (e.g., prostate tumor, etc.) requiring radiotherapy treatment, and OAR 148 a proximal healthy structure or non-target structure (e.g., rectum, bladder, etc.) that might be adversely affected by the treatment. Target 146 is also known as a planning target volume (PTV). Although an example is shown in FIG. 1, the treatment volume may include multiple targets 146 and OARs 148 with complex shapes and sizes. Further, although shown as having a regular shape (e.g., cube), voxel 142 may have any suitable shape (e.g., non-regular). Depending on the desired implementation, radiotherapy treatment planning at block 130 may be performed based on any additional and/or alternative data, such as prescription, disease staging, biologic or radiomic data, genetic data, assay data, biopsy data, past treatment or medical history, any combination thereof, etc.

Based on structure data 140 and dose data 150, treatment plan 156 may be generated to include 2D fluence map data for a set of beam orientations or angles. Each fluence map specifies the intensity and shape (e.g., as determined by a multileaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 156 may include machine control point data (e.g., jaw and leaf positions), volumetric modulated arc therapy (VMAT) trajectory data for controlling a treatment delivery system, etc. In practice, block 130 may be performed based on goal doses prescribed by a clinician (e.g., oncologist, dosimetrist, planner, etc.), such as based on the clinician's experience, the type and extent of the tumor, patient geometry and condition, etc.

At 160 in FIG. 1, treatment delivery is performed during a treatment phase to deliver radiation to the patient according to treatment plan 156. For example, radiotherapy treatment delivery system 160 may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 156. Controller 162 may be used to retrieve treatment plan 156 and control gantry 164, radiation source 166 and radiation beam 168 to deliver radiotherapy treatment according to treatment plan 156.

It should be understood that any suitable radiotherapy treatment delivery system(s) may be used, such as mechanic-arm-based systems, tomotherapy type systems, brachy, sirex spheres, any combination thereof, etc. Additionally, examples of the present disclosure may be applicable to particle delivery systems (e.g., proton, carbon ion, etc.). Such systems may employ either a scattered particle beam that is then shaped by a device akin to an MLC, or a scanning beam of adjustable energy, spot size and dwell time.

Conventionally, radiotherapy treatment planning at block 130 in FIG. 1 is time and labor intensive. For example, it usually requires a team of highly skilled and trained oncologists and dosimetrists to manually delineate structures of interest by drawing contours or segmentations on image data 120. These structures are manually reviewed by a physician, possibly requiring adjustment or re-drawing. In many cases, the segmentation of critical organs can be the most time-consuming part of radiation treatment planning. After the structures are agreed upon, there are additional labor-intensive steps to process the structures to generate a clinically-optimal treatment plan specifying treatment delivery data such as beam orientations and trajectories, as well as corresponding 2D fluence maps. These steps are often complicated by a lack of consensus among different physicians and/or clinical regions as to what constitutes "good" contours or segmentation. In practice, there might be a huge variation in the way structures or segments are drawn by different clinical experts. The variation may result in uncertainty in target volume size and shape, as well as the exact proximity, size and shape of OARs that should receive minimal radiation dose. Even for a particular expert, there might be variation in the way segments are drawn on different days.

According to examples of the present disclosure, artificial intelligence (AI) techniques may be applied to ameliorate various challenges associated with radiotherapy treatment planning. In particular, deep learning engine(s) may be used to automate radiotherapy treatment planning step(s). Throughout the present disclosure, the term "deep learning" may refer generally to a class of approaches that utilizes many layers or stages of nonlinear data processing for feature learning as well as pattern analysis and/or classification. The "deep learning model" may refer to a hierarchy of "layers" of nonlinear data processing that include an input layer, an output layer, and multiple (i.e., two or more) "hidden" layers between the input and output layers. These layers may be trained from end-to-end (e.g., from the input layer to the output layer) to extract feature(s) from an input and classify the feature(s) to produce an output (e.g., classification label or class).

Accordingly, the term "deep learning engine" may refer to any suitable hardware and/or software component(s) of a computer system that are capable of executing algorithms according to any suitable deep learning model(s). Depending on the desired implementation, any suitable deep learning model(s) may be used, such as convolutional neural network, recurrent neural network, deep belief network, or any combination thereof, etc. In practice, a neural network is generally formed using a network of processing elements (called "neurons," "nodes," etc.) that are interconnected via connections (called "synapses," "weights," etc.). For example, convolutional neural networks may be implemented using any suitable architecture(s), such as U-net, LeNet, AlexNet, ResNet, V-net, DenseNet, etc. In this case, a "layer" of a convolutional neural network may be a convolutional layer, pooling layer, rectified linear units (ReLU) layer, fully connected layer, loss layer, etc. In practice, the U-net architecture includes a contracting path (left side) and an expansive path (right side). The contracting path includes repeated application of convolutions, followed by a ReLU layer and max pooling layer. Each step in the expansive path may include upsampling of the feature map followed by convolutions, etc.

Deep learning approaches should be contrasted against machine learning approaches that have been applied to, for example, automatic segmentation. In general, these approaches involve extracting (hand-designed) feature vectors from images, such as for every voxel, etc. Then, the feature vectors may be used as input to a machine learning model that classifies which class each voxel belongs to. However, such machine learning approaches usually do not make use of complete image data and additional constraints may be required. Another challenge is that these approaches rely on a high dimension of hand-designed features in order to accurately predict the class label for each voxel. Solving a high-dimensional classification problem is computationally expensive and requires a large amount of memory. Some approaches use lower dimensional features (e.g., using dimensionality reduction techniques) but they may decrease the prediction accuracy.

Conventionally, there are many challenges associated with training deep learning engines for radiotherapy treatment planning. For example, different planners (e.g., individuals, groups, clinical sites or institutions, networks, etc.) generally have different clinical practices in radiotherapy treatment planning. To train a deep learning according to a specific clinical practice, one option is to develop a specific in-house model. However, it may be difficult to achieve desirable training results without collecting a huge amount of curated training data. Also, while conceptually simple, training deep learning engines generally requires significant technical expertise relating to model architecture(s), optimization, convergence analysis, regularization, etc. These challenges may lead to suboptimal results or, worse, failure to create any working deep learning engines. Such complexity may deter users from training and using deep learning engines for radiotherapy treatment planning, which is undesirable.

Further, there may be intrinsic problem(s) relating to deep learning engines. For example, although a trained deep learning engine may operate consistent with its training data, there is no guarantee that the engine may be generalized to other datasets. In relation to automatic segmentation, this might lead to suboptimal contouring. For example, a breast segmentation model that is trained using data from clinics based in Europe and United States may not be applicable to patient data from other geographic regions. The differences might include average size, weight and shape of the patient population. Additionally, different planners have differing contouring practices which might be driven by different modalities and strategies (e.g., VMAT vs IMRT). As such, a deep learning engine that performs well for one clinic might not be accepted by another.

Continuous Deep Learning

According to examples of the present disclosure, radiotherapy treatment planning may be implemented based on continuous deep learning to improve the performance of deep learning engines. As used herein, the term "continuous deep learning" (also known as "lifelong learning," "incremental learning" and "sequential learning") may refer generally to technique(s) where a deep learning engine is modified or improved throughout its operation based on additional training data. This way, a trained deep learning engine may be modified over time to adapt to the desired clinical practices and/or patient population. By improving the adaptability of deep learning engines, treatment planning outcome may also be improved for patients, such as increasing the tumor control probability and/or reducing the likelihood of health complications or death due to radiation overdose in the healthy structures, etc.

Figure 2:
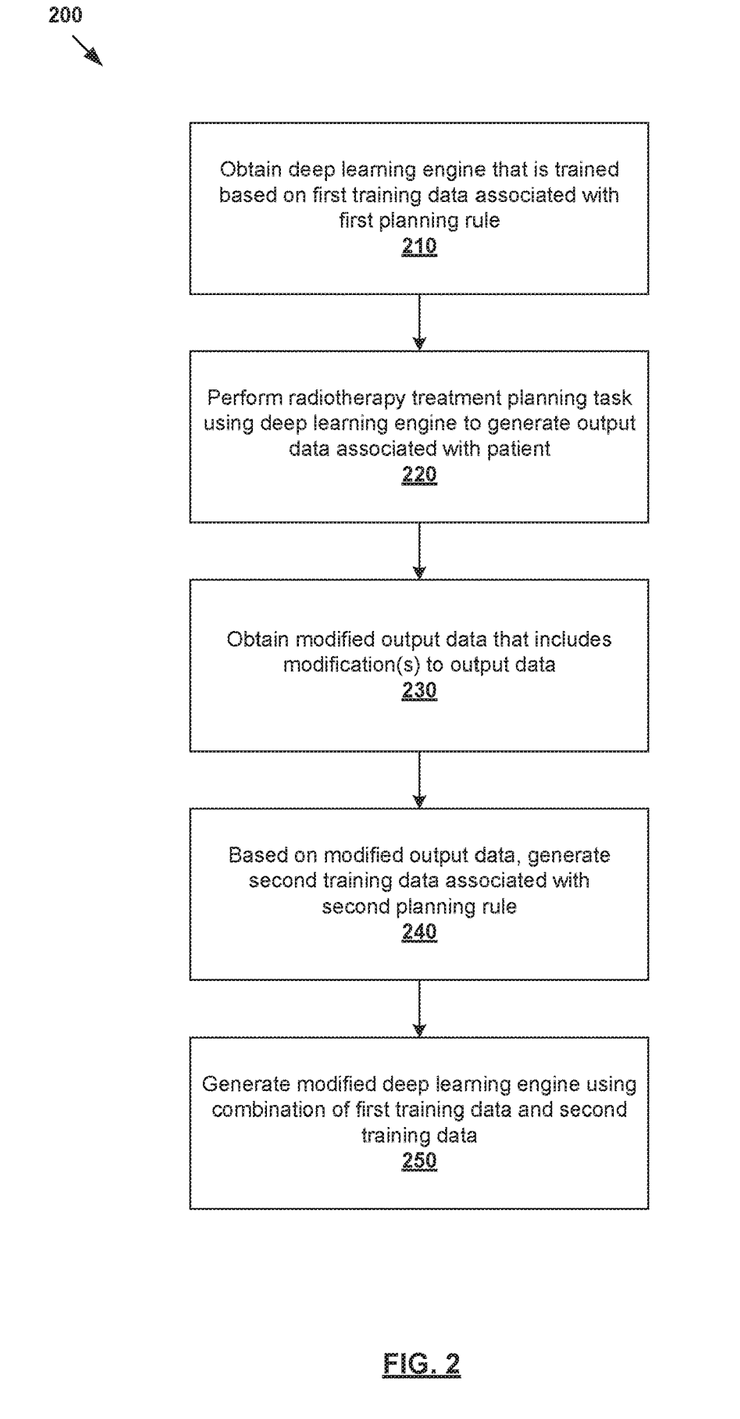
FIG. 2 is a flowchart of an example process for a computer system to perform radiotherapy treatment planning based on continuous deep learning.

In more detail, FIG. 2 is a flowchart illustrating example process 200 for a computer system to perform radiotherapy treatment planning based on continuous deep learning. Example process 200 may include one or more operations, functions, or actions illustrated by one or more blocks, such as 210 to 250. The various blocks may be combined into fewer blocks, divided into additional blocks, and/or eliminated based upon the desired implementation. Example process 200 may be implemented using any suitable computer system(s), an example of which will be discussed using FIG. 9. Some examples will be explained using FIG. 3, which is a schematic diagram illustrating example radiotherapy treatment planning based on continuous deep learning according to the example in FIG. 2.

At 210 in FIG. 2, a deep learning engine (see 320 in FIG. 3) that is trained to perform a radiotherapy treatment planning task may be obtained. Here, the term "obtain" may refer generally to a computer system accessing, or retrieving data and/or computer-readable instructions associated with, deep learning engine 320 from any suitable source (e.g., another computer system), memory or datastore (e.g., local or remote), etc. Deep learning engine 320 may be trained during training phase 301 based on first training data (see 310 in FIG. 3) associated with a first planning rule. As used herein, the term "planning rule" may refer generally to any suitable clinical guideline(s), planning strategy and/or planning practice(s) relating to a particular radiotherapy treatment planning task and/or anatomical site.

At 220 in FIG. 2, deep learning engine 320 may be used to perform the radiotherapy treatment planning task during inference phase 302. For example, based on input data (see 330 in FIG. 3) associated with a particular patient, deep learning engine 320 may perform the radiotherapy treatment planning task to generate output data (see 340 in FIG. 3) associated with the patient. In practice, deep learning engine 320 may be trained to perform any suitable radiotherapy treatment planning task, such as automatic segmentation, dose prediction, treatment delivery data estimation, abnormal organ detection, treatment outcome prediction, or any combination thereof.

In the case of automatic segmentation, deep learning engine 320 may be trained to generate output=structure data (e.g., 140 in FIG. 1) based on input=image data (e.g., 120 in FIG. 1). In the case of dose prediction, engine 320 may be trained to generate output=dose data (e.g., 150 in FIG. 1) based on input=structure data and beam geometry data. In the case of treatment delivery data estimation, engine 320 may be trained to generate output=treatment delivery data (e.g., fluence map data, structure projection data, etc.) based on input=structure data and/or dose data, etc.

At 230 in FIG. 2, modified output data (see 350 in FIG. 3) that includes modification(s) to output data 340 may be obtained. This way, at 240 in FIG. 2, second training data (see 360 in FIG. 3) associated with a second planning rule may be generated. In practice, modified output data 350 may be generated by a planner according to the second planning rule to achieve better treatment planning outcome.

Figure 3:
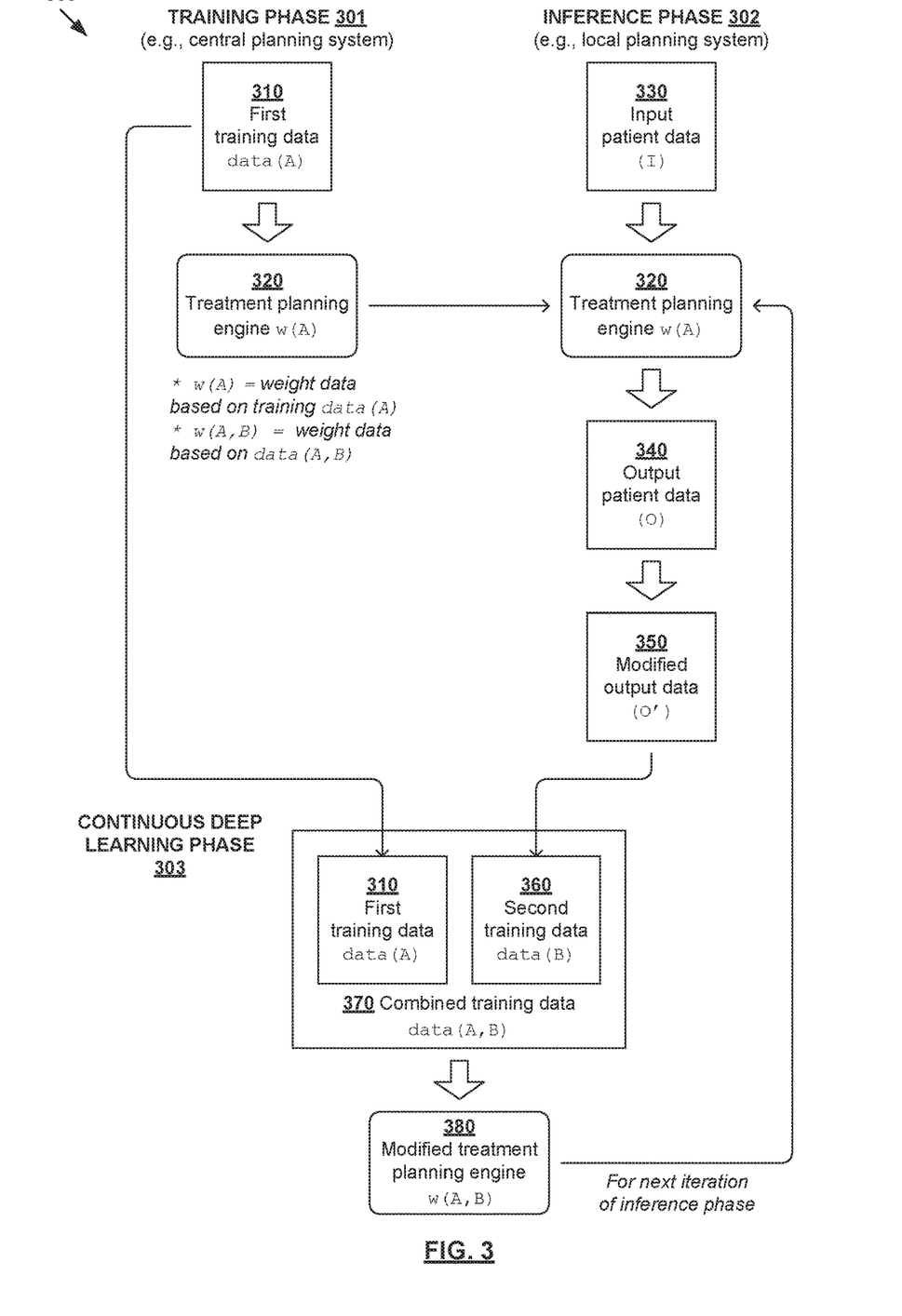
FIG. 3 is a schematic diagram illustrating an example radiotherapy treatment planning based on continuous deep learning according to the example in FIG. 2.

The term "modification" may refer generally to an addition, deletion, correction, change or alteration made to output data. For example, in the case of automatic segmentation (to be discussed using FIG. 4), modified output data 350 may include the following modification(s): a modified segmentation margin around a structure; an extension of a structure in a particular direction; a cut of one part of a structure; a modified cutting plane of a structure; modified margins at different sides of a structure, etc. In relation dose prediction (to be discussed using FIG. 5), modified output data 350 may include the following modification(s): modified organ sparing, modified target coverage, modified target dose prescription, modified normal tissue dose prescription, etc. Any alternative and/or additional modification(s) may be used.

At 250 in FIG. 2, a modified deep learning engine (see 380 in FIG. 3) may be generated by re-training or modifying deep learning engine 320 using a combination (see 370 in FIG. 3) of first training data 310 and second training data 360. Continuous deep learning at block 250 may be performed to facilitate adaptation from the first planning rule to the second planning rule. In the example in FIG. 3, deep learning engine 320 that is trained using first training data 310 (data(A)) may include multiple processing layers associated with weight data (w(A)). In this case, modified deep learning engine 380 that is trained using combined training data 370 (data(A, B)) may include multiple processing layers associated with modified weight data (w(A, B)).

In practice, second training data 360 may represent local, user-generated training data. In contrast, first training data 310 may represent a more general dataset associated with a different planning rule that might have been devised for a different patient population. For example, deep learning engine 320 may be trained according to a planning rule that is more suitable for a particular patient population (e.g., patients in Europe and United States). During continuous deep learning phase 303, improvement may be made to adapt deep learning engine 320 to a different planning rule for a different patient population (e.g., patients in East Asia).

The combination or mixing ratio between first training data 310 and second training data 360 may be adjusted over time. Initially, there may be more first training data 310 compared to second training data 360. As more local training data becomes available, the ratio of second training data 360 increases. It should be noted that first training data 310 may be included fully or partially in combined training data 370. As will be discussed further using FIG. 6 and FIG. 7, second training data 360 may be generated using a local planning system operated by a planner. In this case, second training data 360 may represent additional training data that is generated by a planner according to a preferred second planning rule.

Examples of the present disclosure may be implemented to ameliorate various challenges associated with training deep learning engines for radiotherapy treatment planning. In practice, training phase 301 may be implemented by a central planning system (to be discussed using FIG. 6 and FIG. 7). Inference phase 302 may be implemented "locally" at a clinical site, where output data 340 of deep learning engine 320 may be improved through user corrections. Each time a planner generates modified output data 350, additional second training data 360 may be used for continuous training of the deep learning engine. As more corrections or modifications become available, deep learning engine 320/380 may be adapted to local needs.

Further, it is not necessary for users to have extensive knowledge about deep learning model architecture(s), etc. Using deep learning engine 320 that is already stable as a starting point, users would not have to worry so much about technical issues, such as convergence, local minima or poor weight initializations. As such, it is not necessary to train deep learning engine 320 from scratch, especially when only a limited amount of local training data (e.g., limited in amount or variations compared to first training data 310). Instead, users may take advantage of the better-quality first training data 310 (e.g., more data, availability of expert-curated data, more variations, etc.) used to train deep learning engine 320 during training phase 301. As such, the risk of achieving suboptimal training results during training phase 301 may also be reduced.

Various examples will be discussed below using FIG. 4 to FIG. 9. In particular, an example automatic segmentation will be discussed using FIG. 4, an example dose prediction using FIG. 5, an example deployment using FIG. 6, an example treatment plan using FIG. 7 and an example computer system using FIG. 8.

Automatic Segmentation

Figure 4:
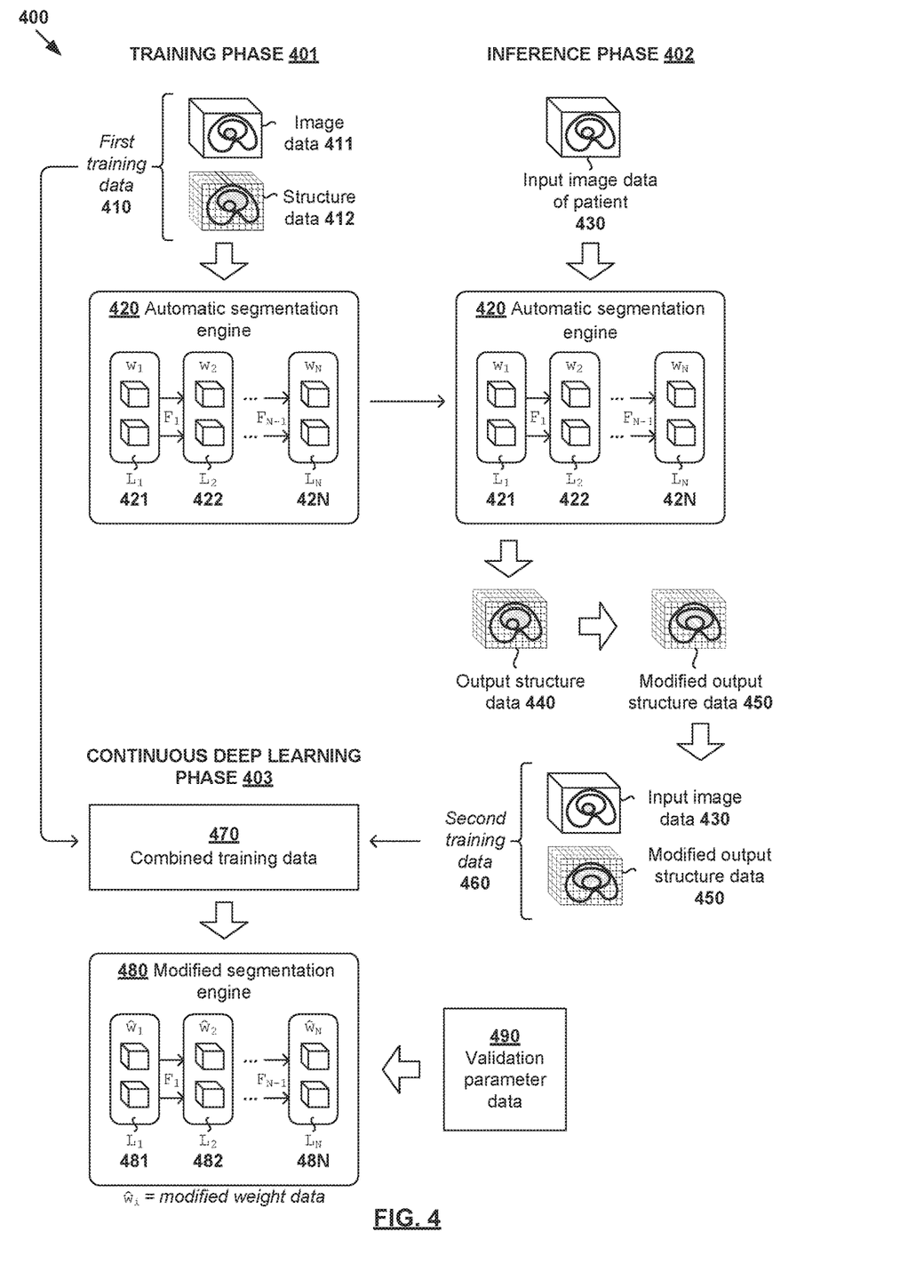
FIG. 4 is a schematic diagram illustrating an example automatic segmentation based on continuous deep learning.

FIG. 4 is a schematic diagram illustrating example automatic segmentation based on continuous deep learning. In the example in FIG. 4, deep learning engine 420 (also referred to as "segmentation engine" below) may be trained using first training data 410 during training phase 401; applied to perform automatic segmentation during inference phase 402; and re-trained or improved during continuous deep learning phase 403. In practice, the output of automatic segmentation may be used for abnormal organ detection, dose prediction, treatment delivery data estimation, etc.

(a) Training Phase (See 401 in FIG. 4)

During training phase 401, segmentation engine 420 may be trained to map training image data 411 (i.e., input) to training structure data 412 (i.e., output). In practice, image data 411 may include 2D or 3D images of a patient's anatomical site, and captured using any suitable imaging modality or modalities. Structure data 412 may identify any suitable contour, shape, size and/or location of structure(s) from image data 411. Example structures may include target(s), OAR(s) or any other structure of interest (e.g., tissue, bone) of the anatomical site. Depending on the desired implementation, structure data 412 may identify multiple targets and OARs of any suitable shapes and sizes.

For example, in relation to prostate cancer, image data 411 may include images of site=prostate region. In this case, structure data 412 may identify a target representing each patient's prostate, and OARs representing proximal healthy structures such as rectum and bladder. In relation to lung cancer treatment, image data 411 may include images of a lung region. In this case, structure data 412 may identify a target representing cancerous lung tissue, and an OAR representing proximal healthy lung tissue, esophagus, heart, etc. In relation to brain cancer, image data 411 may include images of a brain region. Structure data 412 may identify a target representing a brain tumor, and an OAR representing a proximal optic nerve, brain stem, etc.

First training data 410 may be extracted from past treatment plans developed for multiple past patients according to any desirable planning rule, and/or obtained from any suitable source(s) (e.g., system provider, hospital, patient database, etc.). First training data 410 may be pre-processed using any suitable data augmentation approach (e.g., rotation, flipping, translation, scaling, noise addition, cropping, any combination thereof, etc.) to produce a new dataset with modified properties to improve model generalization using ground truth. In practice, a 3D volume of the patient that will be subjected to radiation is known as a treatment volume, which may be divided into multiple smaller volume-pixels (voxels). In this case, structure data 412 may specify a class label (e.g., "target," "OAR," etc.) associated with each voxel in the 3D volume.

Any suitable deep learning model(s) may be used. For example in FIG. 4, segmentation engine 420 includes multiple (N>1) processing blocks or layers that are each labelled $L_i$, where i=1, N (see 421-42N). In this case, training phase 401 may involve finding weight data (denoted as $w_i$ for $L_i$) that minimizes a training error between training structure data 412, and estimated structure data (not shown for simplicity) generated by segmentation engine 420. Training phase 401 may also involve finding other parameters or hyperparameters, such as parameters relating to an activation function, etc. The training process may be guided by estimating losses associated with the classification error. A simple example of a loss function would be mean squared error between true and predicted outcome, but the loss function could have more complex formulas. For example, the loss function itself might be a deep neural network. This loss can be estimated from the output of the model, or from any discrete point within the model.

Weight data $w_i$ for the $i^{th}$ layer may be a scalar or multi-dimensional vector. In the case of convolutional neural networks, the $i^{th}$ layer ($L_i$) may be a convolutional layer that is configured to extract feature data ($F_i$) from training data 410 or the output of the $(i-1)^{th}$ layer ($L_{i-1}$) using convolution operations. For example, the first layer ($L_1$) processes input image data 411 to generate first feature data ($F_1$). The second layer ($L_2$) processes the first feature data ($F_1$) to generate second feature data ($F_2$), and so on. Feature extraction at the $i^{th}$ layer ($L_1$) may involve applying convolutional filter(s) or kernel(s) to overlapping sites of its input to learn corresponding weight data ($w_1$).

The feature data ($F_i$) generated by the $i^{th}$ layer may include a 2D feature map for 2D image data, or a 3D feature map for 3D image data. Feature data ($F_i$) may specify any suitable anatomical feature(s), such as borders, distance to centroid, distance to midline, distance to skin, distance from bone, laterality, presence of vertical and/or horizontal lines, shape-related parameter(s), texture types, any combination thereof, etc. This automatic feature extraction approach should be distinguished from conventional approaches that rely on hand-designed features.

(b) Inference Phase (See 402 in FIG. 4)

At 430 and 440 in FIG. 4, a planner may access trained segmentation engine 420 to perform automatic segmentation for a particular patient. Input image data 430 associated with that patient is processed using multiple layers 421-42N of segmentation engine 420 to extract feature data ($F_i$ for layer $L_i$). The aim is to generate output structure data 440 based on the feature data. Output structure data 440 may identify any suitable contour, shape, size and/or location of structure(s) detectable from input image data 430.

At 450 in FIG. 4, output structure data 440 may be modified based on any suitable segmentation rule(s) desired by the user to achieve a preferred segmentation outcome. In relation to automatic segmentation, modified output structure data 450 may include the following modification(s): a modified segmentation margin (e.g., from 2 mm to 4 mm) around a contoured structure; an extension of a structure in one direction; a cut of one part of a structure; a modified cutting plane of a structure (e.g., spinal cord); modified margins at different sides of a structure (e.g., more margin on inferior sides compared to superior sides of an organ), any combination thereof, etc.

At 460 in FIG. 4, second training data 460 may be generated to facilitate subsequent improvement of segmentation engine 420. For example, second training data 460 may include input image data 430 and corresponding modified structure data 450, as well as any additional training data (not shown for simplicity). Compared to first training data 410, second training data 460 may represent user-generated training data that is designed to train segmentation engine 420 to achieve a more desirable segmentation outcome.

(c) Continuous Deep Learning Phase (See 403 in FIG. 4)

At 470 in FIG. 4, combined training data 470 may be generated using a combination of first training data 410 and second training data 460. This way, modified segmentation engine 480 may be generated by re-training or modifying segmentation engine 420 based on combined training data 470. In the example in FIG. 4, modified segmentation engine 480 may include multiple (N>1) processing layers ($L_i$) with associated modified weight data ($\hat{w}_i$), where i=1, ..., N (see 481-48N). In practice, any suitable mixing or combination ratio may be used for combined training data 470. The mixing ratio is a parameter that may evolve over time as more local (user-generated) training data becomes available.

Any suitable continuous deep learning approach may be used. In one example, segmentation engine 420 may be trained for multiple epochs each time user-generated segmentation is added to second training data 460. In another example, segmentation engine 420 may be re-trained from scratch in intervals (e.g., once a day, once a week or any other interval), such as using computing resources that are locally available at a clinical site, etc. Further, a case weight may be assigned to each case in combined training data 470. Using an equal weighting approach, all training cases are treated equally. For example, if there are 1000 cases in first training data 410 and 200 cases in second training data 460, all training cases may be assigned with the same case weight. Alternatively, some training cases may be assigned with a higher case weight, such as those that are considered to be better quality.

At 490 in FIG. 4, modified segmentation engine 480 may be evaluated based on any suitable validation parameter data 490 and any user-provided validation set. Validation parameter data 490 may include any suitable parameter(s), such as dice score, average surface difference (measuring the error of the contoured surface location relative to the ground truth), Hausdorff distance, accuracy, specificity, overlap volumes (e.g., if volumes are allowed to be overlapped), number of extra slices above a set plane in the image set, Jaccard index (e.g., for comparing the similarity and diversity of sample sets), any combination thereof, etc. In practice, validation may be performed to ensure that the quality of modified segmentation engine 480 is better than, or at least the same as, segmentation engine 420. Once validated, modified segmentation engine 480 may be used to perform automatic segmentation for a patient during the next iteration of inference phase 402. If modification is made to output data generated by modified segmentation engine 480, continuous deep learning phase 403 may be repeated for further improvement.

Depending on the desired implementation, the validation process may be unsupervised, supervised or a combination of both. According to the unsupervised approach, validation of modified engine 480 may be performed based on (a) a validation dataset provided by a system provider (e.g., Varian Medical Systems), or (b) a validation dataset provided by a user (e.g., clinic). In both options, the goal is to ensure that the quality of modified engine 480 improves (or at least does not degrade substantially) over initial engine 420. Also, the quality of modified engine 480 may be assessed using any suitable validation parameter data 490, such as an average or median of a metric over the validation set.

For option (a) of unsupervised learning, the validation criterion may be relaxed when the user (e.g., clinic) is able to provide sufficient training data. For option (b), the validation set may be a random selection of patients; a selection based on metrics from initial engine 420 (validated against outliers) or a selection performed by the user. When validating against outliers, the general idea is to focus on the cases that are specific to the user but may not present in first training data 410. These outliers may be weighted more during continuous deep learning phase 403. Alternatively, according to the supervised learning approach, a user may be notified in response to determination that the validation process does not produce a clear result (i.e., modified engine 480 fails validation using option (a) or (b) above). In this case, the user may review second training data 460, such as cases for which the model quality decreases; selected or outlier cases; and metrics of the evaluated patients.

After the validation is performed, there may be several possible scenarios. In a first scenario where modified engine 480 improves over initial engine 420, modified engine 480 may be deployed automatically and the user notified. Alternatively, in a second scenario, the user may be notified and asked to manually review cases for which modified engine 480 performs worse based on validation parameter data 490 used during validation. The user may then make a decision as to whether to deploy modified engine 480 for the next iteration of the inference phase.

In a third scenario where modified engine 480 does not improve over initial engine 420, modified engine 480 will not be deployed automatically. Instead, the user may be provided with an interface to inspect any new training data 460. The inspection may identify whether the data quality is sufficient, or whether it is related to different patient anatomy, plan type, etc. Once inspected, the user may choose to reject training data 460, either fully or partially. Another option is that the training process may be automatically modified to create a new modified engine, such as by increasing the training duration, the use of hyper search on model parameters or different sample strategies. After training, the modified engine may enter the validation pipeline. Instead of the options discussed here, the data collection and retraining process may also be maintained, in that a new training process is initiated once sufficient new data is collected. There may be a chance that the engine improves once new training data is available.

Dose Prediction and Other Planning Tasks

Figure 5:
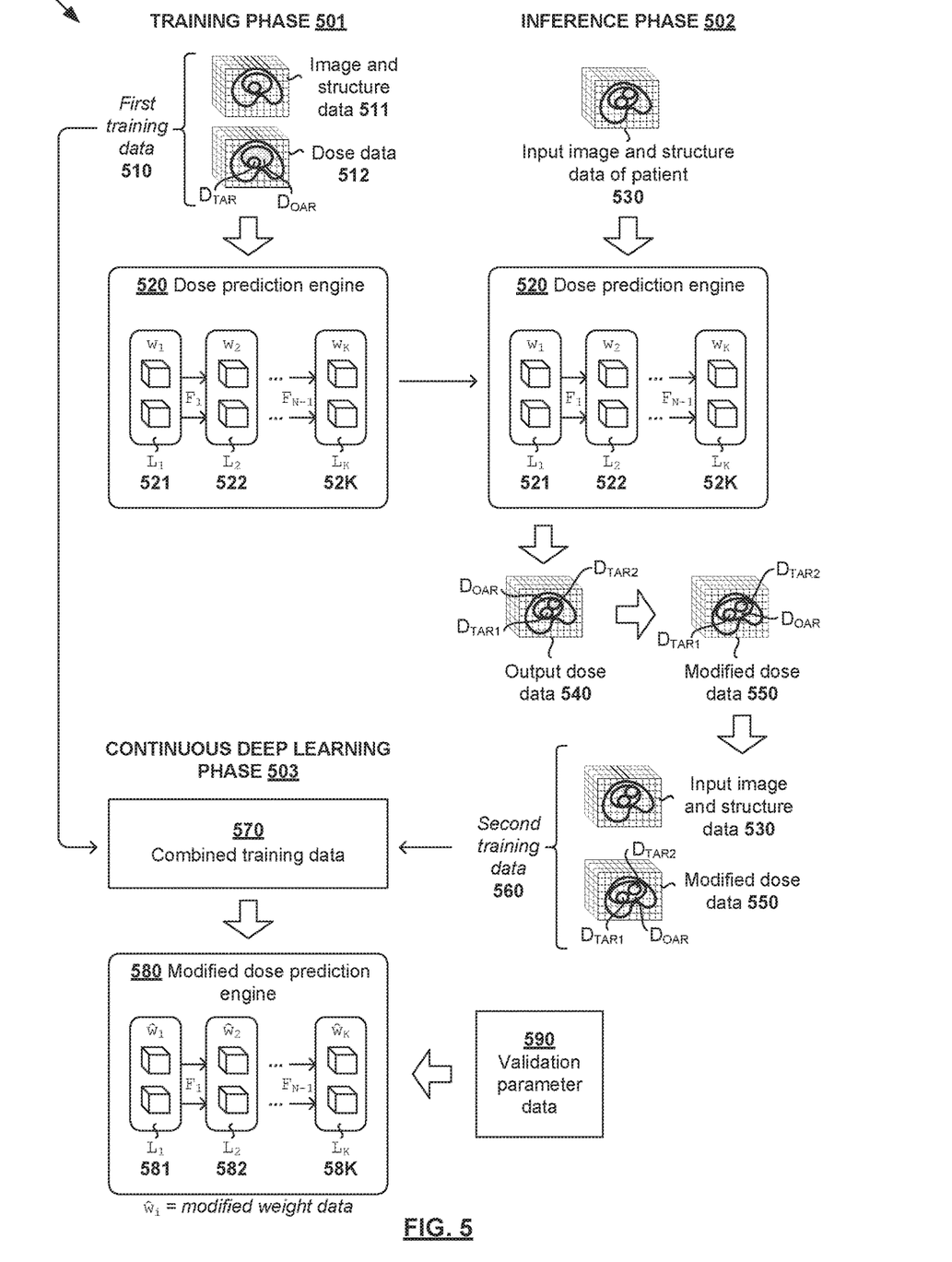
FIG. 5 is a schematic diagram illustrating an example dose prediction based on continuous deep learning.

FIG. 5 is a schematic diagram illustrating example dose prediction based on continuous deep learning. In this example, deep learning engine 520 (i.e., "dose prediction engine" below) may be trained using first training data 510 during training phase 501; applied to perform dose prediction during inference phase 502; and modified during continuous deep learning phase 503.

During training phase (see 501 in FIG. 5), first training data 510 may be used to train dose prediction engine 520. First training data 510 may include image and structure data 511 (i.e., training input) and dose data 512 (i.e., training output) associated with multiple past patients. Dose data 512 (e.g., 3D dose data) may specify dose distributions for a target (denoted "$D_{TAR}$") and an OAR (denoted "$D_{OAR}$"). For example, in relation to prostate cancer, dose data 512 may specify dose distributions for a target representing the patient's prostate, and an OAR representing a proximal healthy structure such as rectum or bladder. In practice, dose data 512 may specify the dose distributions for the whole 3D volume, not just the target and OAR volumes. Dose data 512 may include spatial biological effect data (e.g., fractionation corrected dose) and/or cover only part of the treatment volume. Any additional input data may be used to train dose prediction engine 520, such as beam geometry data associated with the treatment delivery system, photon energy used during treatment, treatment type (e.g., stereotactic, photon, proton, electron, etc.).

During inference phase (see 502 in FIG. 5), dose prediction engine 520 may be used to generate output dose data 540 based on input image and structure data 530 associated with a particular patient. Output dose data 540 may be estimated by processing input data 530 using multiple (K>1) processing layers that are each labelled as $L_1$ with associated weight data $w_i$, where i=1, . . . , K (see 541-54K). Dose data 540 may specify dose distributions for an OAR (denoted "$D_{OAR}$") and multiple targets (e.g., $D_{TAR1}$ and $D_{TAR2}$). Dose data 540 may specify the dose distributions for the whole 3D volume, not just the target and OAR volumes. Modification(s) may then be made to generate modified output dose data 550 based on any suitable dose prediction rule(s) preferred by the planner. The modification(s) may include modified organ sparing (e.g., to emphasize the importance of some organs more than others), modified target coverage, modified target dose prescription, and modified normal tissue dose. Additionally or alternatively, modification(s) may be related to treatment techniques (e.g., IMRT, VMAT, etc.), field geometry, machine specification (e.g., energy and field shape, clinical practices for field placements), etc.

During continuous deep learning phase (see 503 in FIG. 5), a combination of first training data 510 (i.e., used during training phase 501) and second training data 560 (i.e., generated based on modified dose data 550) may be used to improve dose prediction engine 520. Modified dose prediction engine 580 may include multiple (K>1) processing layers ($L_1$) with associated modified weight data ($\hat{w}_i$), where i=1, . . . , K (see 581-58K). Next, modified dose prediction engine 580 may be validated based on any suitable validation parameter data 590 and validation dataset. This is to ensure that the dose prediction quality is improved (or at least maintained) after continuous deep learning. Example validation parameter data and various validation approaches (e.g., supervised, unsupervised, automatic deployment, user's manual inspection, etc.) discussed with respect to automatic segmentation in FIG. 4 are also applicable here and will not be repeated for brevity.

Once validated and approved, modified dose prediction engine 580 may be deployed for use in the next iteration of inference phase 502. If modification is made to output dose data generated by modified engine 580, continuous deep learning phase 503 may be repeated for further improvement. Besides automatic segmentation in FIG. 4 and dose prediction in FIG. 5, continuous deep learning may be implemented for other radiotherapy treatment planning tasks, such as treatment delivery data estimation, treatment outcome prediction, etc. The estimated treatment delivery data (i.e., output data) may include structure projection data, fluence map data, etc. For example, a deep learning engine may be trained to perform structure projection data, such as based on image data, structure data, dose data, or any combination thereof. The structure projection data may include data relating to beam orientations and machine trajectories for a treatment delivery system.

In another example, a deep learning engine may be trained to perform fluence map estimation, such as 2D fluence maps for a set of beam orientations or trajectories, machine control point data (e.g., jaw and leaf positions, gantry and couch positions), etc. Fluence maps will be explained further using FIG. 8. Any additional and/or alternative training data may be used, such as field geometry data, monitor units (amount of radiation counted by machine), quality of plan estimate (acceptable or not), daily dose prescription (output), field size or other machine parameters, couch positions parameters or isocenter position within patient, treatment strategy (use movement control mechanism or not, boost or no boost), treat or no treat decision, etc.

Example Deployment

Examples of the present disclosure may be deployed in any suitable manner, such as a standalone system, web-based planning-as-a-service (PaaS) system, etc. An example will be explained below using FIG. 6, which is a schematic diagram illustrating example network environment 600 in which radiotherapy treatment planning based on continuous deep learning may be implemented.

Network environment 600 includes a central planning system (see 610 in FIG. 6) that is in communication with multiple local planning systems (see 611-614) via any suitable physical network. Local planning systems may be each operated by a planner at a particular planning site. Using M=4 planners in FIG. 6, a first planner ("P1") operates first local planning system 611, second planner ("P2") operates second local planning system 612, third planner ("P3") operates third local planning system 613, and fourth planner ("P4") operates fourth local planning system 614.

Figure 6:
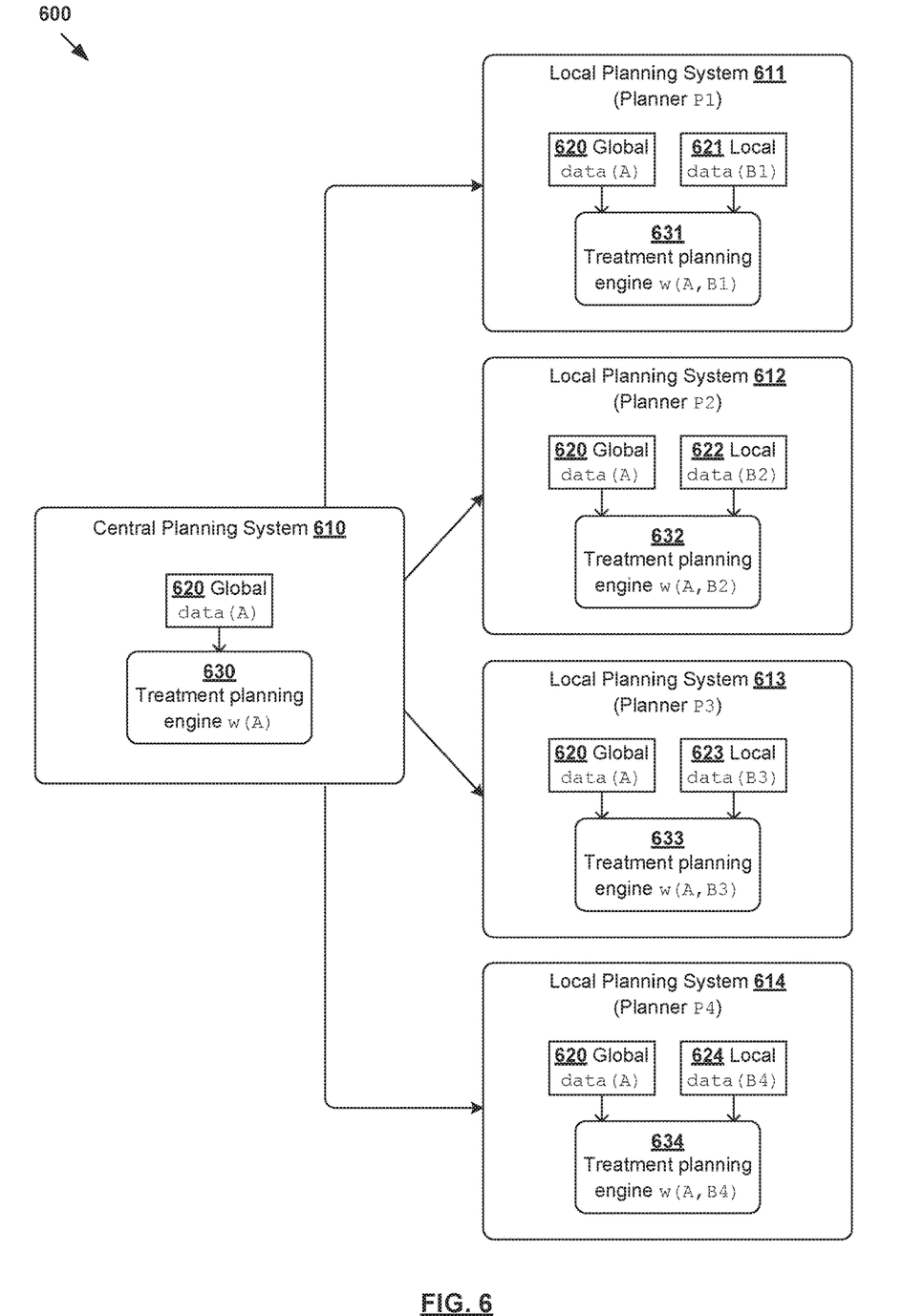
FIG. 6 is a schematic diagram illustrating an example network environment in which radiotherapy treatment planning based on continuous deep learning may be implemented.

Here, the term "local" may refer generally to client-side data and/or element(s) associated with a particular planner and/or local planning system. The term "global" may refer generally to data and/or element(s) associated with central planning system 610 that is accessible by multiple planners through respective local planning systems 611-614. In practice, various functionalities of local planning systems 611-614 may be implemented using standalone systems at respective planning sites. Additionally or alternatively, various functionalities of local planning systems 611-614 may be supported by central planning system 610.

According to the examples in FIG. 1 to FIG. 5, training data 620 (denoted as global data(A)) may be used to train initial treatment planning engine 630 during training phase 301/401/501. Treatment planning engine 630 that includes multiple processing layers associated with weight data (denoted as w(A)) may then be further improved using respective local planning systems 611-614. Treatment planning engine 630 may also be associated with any additional engine parameter data, such as parameters of an activation function, etc. At first local planning system 611, treatment planning engine 630 may be improved by performing continuous deep learning based on a combination of global or public training data 620 (i.e., data(A)), and local or private training data 621 (i.e., data(B1)). The improvement results in modified treatment planning engine 631 associated with modified weight data denoted as w(A, B1).

At second local planning system 612, treatment planning engine 630 may be modified using a combination of data(A) 620, and data(B2) 622 generated by the second planner according to preferred planning rule(s). The continuous deep learning results in modified engine 632. At third local planning system 613, a combination of data(A) 620, and data(B3) 623 associated with the third planner may be used to generate modified engine 633. Finally, at fourth local planning system 613, a combination of data(A) 620, and data(B4) 624 associated with the fourth planner may be used to generate modified engine 634. It should be understood that data(A) may be used fully or partially during the continuous deep learning phase.

Compared to treatment planning engine 630 with weight data w(A), modified treatment planning engines 631-634 are associated with modified weight data denoted as w(A, B1), w(A, B2), w(A, B3) and w(A, B4), respectively. This way, each planner may take advantage of the initial training of treatment planning engine 630 based on training data 620 before adapting it to better satisfy their local needs, styles and requirements. This is especially beneficial when the planners do not have the required technical expertise and/or sufficient local training data 621-624 to train their own in-house engine or model. As more local training data 621-624 becomes available, modified treatment planning engines 631-634 may be improved incrementally over time to achieve a better treatment planning outcome for the respective planners.

In practice, deep transfer learning techniques may be used to facilitate continuous learning of treatment planning engine 630 by respective local planning systems 611-614 in FIG. 6. Here, the term "deep transfer learning" may refer generally to technique(s) where one deep learning engine (see 630) is adapted or re-purposed (fully or partially) as a starting point for another deep learning engine (see 631-634). In one example, deep transfer learning represents an optimization strategy that facilitates faster progress or improved performance during the training process. This way, the knowledge learned by (global) treatment planning engine 630 may be leveraged by local planning systems 611-614 and transferred to respective (local) engines 631-634. As a variant of the example in FIG. 6, local planning systems 611-614 may have access to treatment planning engine 630, but not global data(A) used during training. In this case, continuous deep learning may be performed by re-training treatment planning engine 630 using respective local data(B1) to data(B4) to generate respective modified engines 631-634.

Example Treatment Plan

Figure 7:
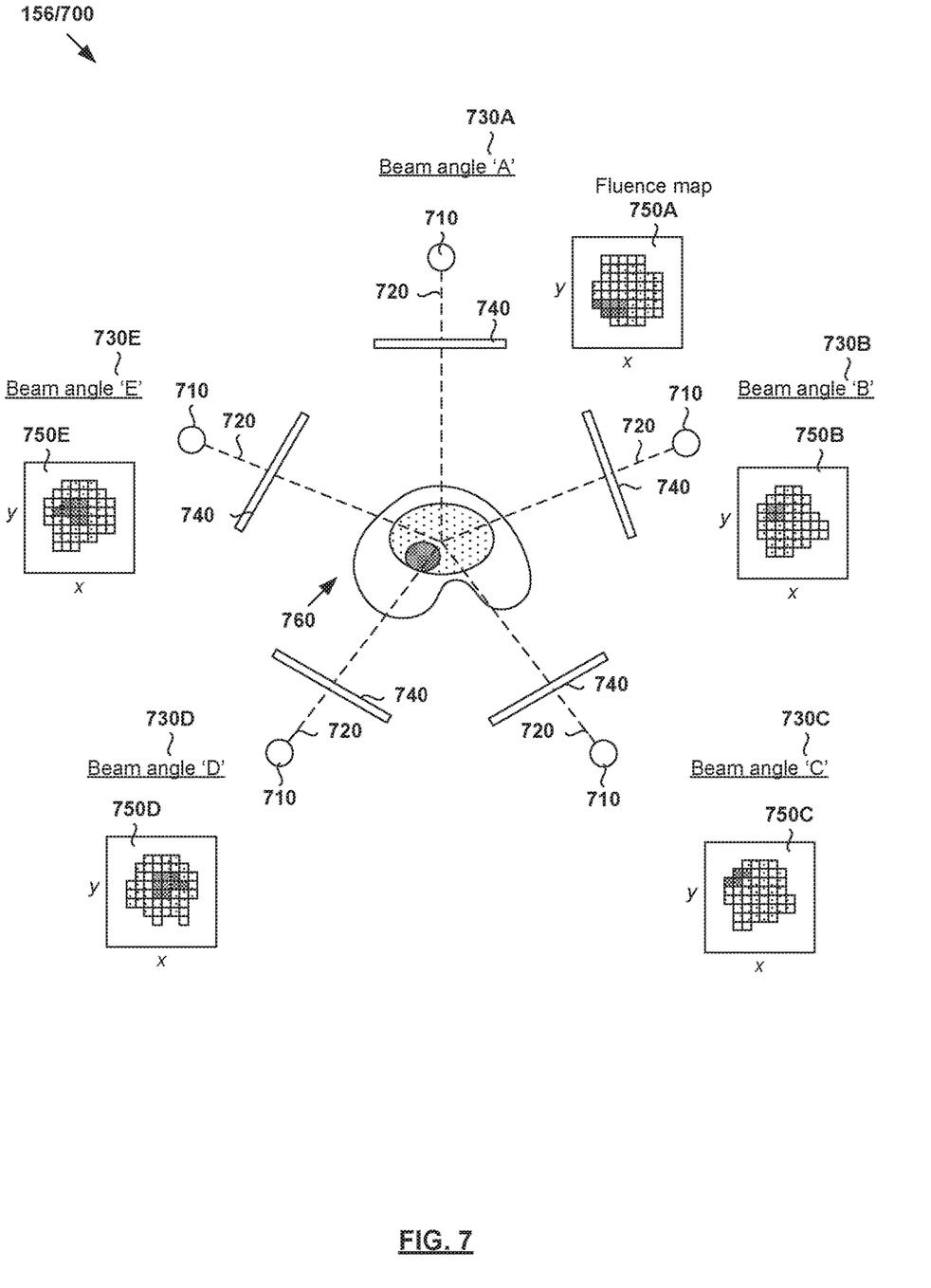
FIG. 7 is a schematic diagram of an example treatment plan for treatment delivery.

During radiotherapy treatment planning, treatment plan 156/900 may be generated based on structure data and/or dose data generated using treatment planning engine discussed above. For example, FIG. 7 is a schematic diagram of example treatment plan 156/700 generated or improved based on output data in the examples in FIG. 1 to FIG. 7. Treatment plan 156 may be delivered using any suitable treatment delivery system that includes radiation source 710 to project radiation beam 720 onto treatment volume 760 representing the patient's anatomy at various beam angles 730.

Although not shown in FIG. 7 for simplicity, radiation source 710 may include a linear accelerator to accelerate radiation beam 720 and a collimator (e.g., MLC) to modify or modulate radiation beam 720. In another example, radiation beam 720 may be modulated by scanning it across a target patient in a specific pattern with various energies and dwell times (e.g., as in proton therapy). A controller (e.g., computer system) may be used to control the operation of radiation source 720 according to treatment plan 156.

During treatment delivery, radiation source 710 may be rotatable using a gantry around a patient, or the patient may be rotated (as in some proton radiotherapy solutions) to emit radiation beam 720 at various beam orientations or angles relative to the patient. For example, five equally-spaced beam angles 730A-E (also labelled "A," "B," "C," "D" and "E") may be selected using a deep learning engine configured to perform treatment delivery data estimation. In practice, any suitable number of beam and/or table or chair angles 730 (e.g., five, seven, etc.) may be selected. At each beam angle, radiation beam 720 is associated with fluence plane 740 (also known as an intersection plane) situated outside the patient envelope along a beam axis extending from radiation source 710 to treatment volume 760. As shown in FIG. 7, fluence plane 740 is generally at a known distance from the isocenter.

In addition to beam angles 730A-E, fluence parameters of radiation beam 720 are required for treatment delivery. The term "fluence parameters" may refer generally to characteristics of radiation beam 720, such as its intensity profile as represented using fluence maps (e.g., 750A-E for corresponding beam angles 730A-E). Each fluence map (e.g., 750A) represents the intensity of radiation beam 720 at each point on fluence plane 740 at a particular beam angle (e.g., 730A). Treatment delivery may then be performed according to fluence maps 750A-E, such as using IMRT, etc. The radiation dose deposited according to fluence maps 750A-E should, as much as possible, correspond to the treatment plan generated according to examples of the present disclosure.

Computer System

Figure 8:
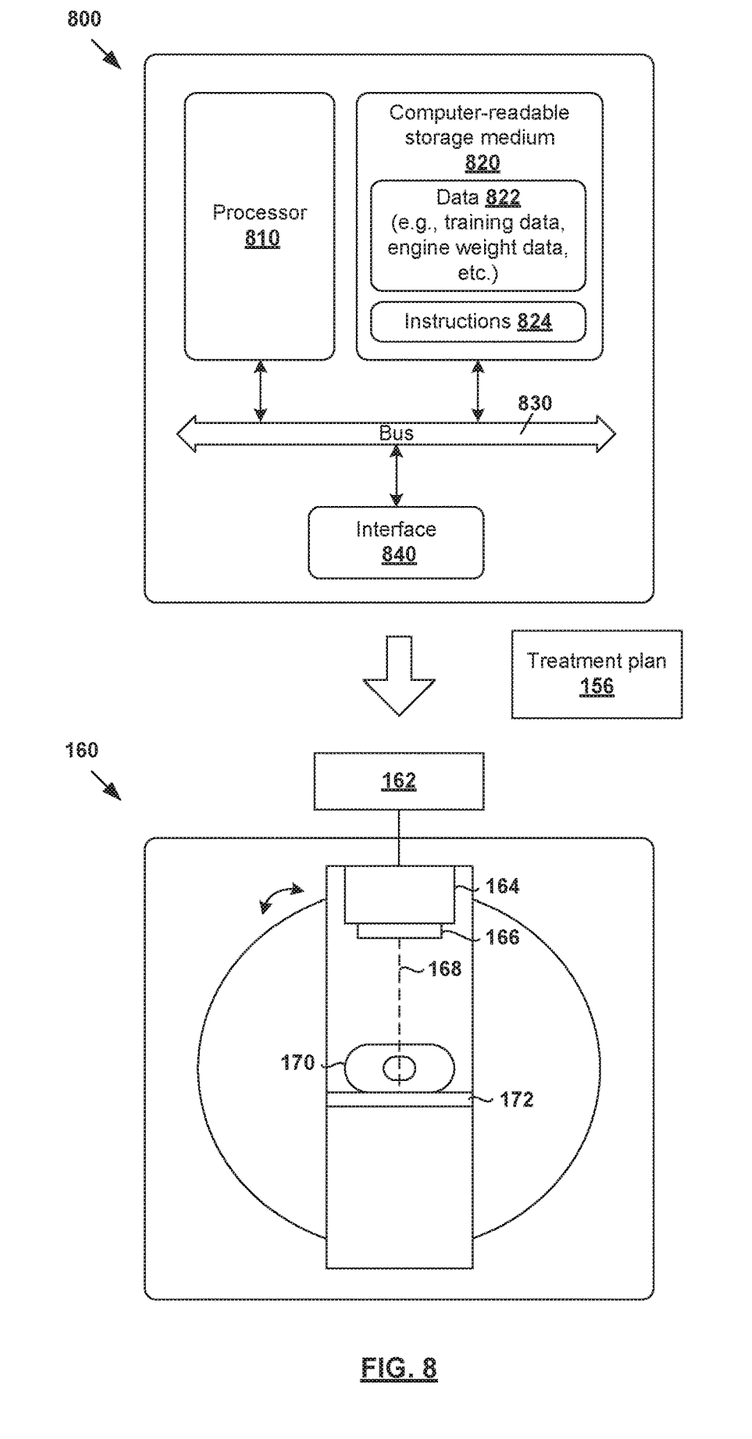
FIG. 8 is a schematic diagram of an example computer system to perform radiotherapy treatment planning based on continuous deep learning.

The above examples can be implemented by hardware, software or firmware or a combination thereof. FIG. 8 is a schematic diagram of example computer system 800 for radiotherapy treatment planning based on continuous learning. In this example, computer system 805 (also known as a treatment planning system) may include processor 810, computer-readable storage medium 820, interface 840 to interface with radiotherapy treatment delivery system 160, and bus 830 that facilitates communication among these illustrated components and other components.

Processor 810 is to perform processes described herein with reference to FIG. 1 to FIG. 7. Computer-readable storage medium 820 may store any suitable information 822, such as information relating to training data, deep learning engines, weight data, input data, output data, etc. Computer-readable storage medium 820 may further store computer-readable instructions 824 which, in response to execution by processor 810, cause processor 810 to perform processes described herein. Treatment may be delivered according to treatment plan 156 using treatment planning system 160 explained using FIG. 1, the description of which will not be repeated here for brevity. In practice, computer system 800 may be part of a computation cluster that includes multiple computer systems. Computer system 800 may include any alternative and/or additional component(s), such as graphics processing unit (GPU), message queues for communication, blob storage or databases, load balancer(s), specialized circuits, etc. Computer system 800 may be deployed in any suitable manner, including a service-type deployment in an on-premise cloud infrastructure, public cloud infrastructure, a combination thereof, etc.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system to perform radiotherapy treatment planning based on continuous deep learning, wherein the method comprises:
   obtaining, by the computer system, a deep learning engine that is trained to perform a radiotherapy treatment planning task based on first training data associated with a first planning rule devised for a first set of patients, wherein the first training data represents data of the first set of patients;
   based on input data associated with a first particular patient from a second set of patients, performing, by the computer system, the radiotherapy treatment planning task using the deep learning engine to generate first output data associated with the first particular patient;
   obtaining, by the computer system, modified output data that includes one or more modifications to the output data generated by the deep learning engine, wherein the modified output data is generated based on a second planning rule devised for the second set of patients;
   based on the modified output data, generating, by the computer system, second training data associated with the second planning rule, wherein the second training data includes the modified output data;
   generating, by the computer system, a modified deep learning engine by re-training the deep learning engine using a combination of the first training data and the second training data, wherein the modified deep learning engine is configured to generate output data for the second set of patients; and
   performing, by the computer system, the radiotherapy treatment planning task using the modified deep learning engine to generate second output data associated with a second particular patient from the second set of patients based on input data associated with the second particular patient.

2. The method of claim 1, wherein generating the modified deep learning engine comprises:
   generating a set of modified weight data associated with multiple processing layers of the modified deep learning engine by modifying weight data associated with multiple processing layers of the deep learning engine.

3. The method of claim 1, wherein obtaining the deep learning engine comprises:
   obtaining the deep learning engine from a central planning system that is configured to train the deep learning engine based on the first training data, wherein the first training data represents global training data, and the second training data represents local training data accessible by the computer system.

4. The method of claim 1, wherein obtaining the modified output data comprises:
   obtaining the modified output data that includes the one or more modifications made by a particular planner according to the second planning rule.

5. The method of claim 1, wherein performing the radiotherapy treatment planning task comprises one of the following:
   performing automatic segmentation to generate output structure data based on input image data associated with the particular patient;
   performing dose prediction to generate output dose data based on input image data and input structure data associated with the particular patient; and
   performing treatment delivery data prediction to generate treatment delivery data based on input dose data associated with the particular patient.

6. The method of claim 5, wherein obtaining the modified output data comprises:
   obtaining modified output structure data that includes at least one of the following modifications: a modified segmentation margin around a structure; an extension of a structure in a particular direction; a cut of one part of a structure; a modified cutting plane of a structure; and modified margins at different sides of a structure.

7. The method of claim 5, wherein obtaining the modified output data comprises:
obtaining modified output dose data that includes at least one of the following modifications: modified organ sparing, modified target coverage, modified target dose prescription, and modified normal tissue dose prescription.

8. A non-transitory computer-readable storage medium that includes a set of instructions which, in response to execution by a processor of a computer system, cause the processor to perform a method of radiotherapy treatment planning based on continuous deep learning, wherein the method comprises:
obtaining, by the computer system, a deep learning engine that is trained to perform a radiotherapy treatment planning task based on first training data associated with a first planning rule devised for a first set of patients, wherein the first training data represents data of the first set of patients;
based on input data associated with a first particular patient from a second set of patients, performing, by the computer system, the radiotherapy treatment planning task using the deep learning engine to generate first output data associated with the first particular patient;
obtaining, by the computer system, modified output data that includes one or more modifications to the output data generated by the deep learning engine, wherein the modified output data is generated based on a second planning rule devised for the second set of patients;
based on the modified output data, generating, by the computer system, second training data associated with the second planning rule, wherein the second training data includes the modified output data;
generating, by the computer system, a modified deep learning engine by re-training the deep learning engine using a combination of the first training data and the second training data, wherein the modified deep learning engine is configured to generate output data for the second set of patients; and
performing, by the computer system, the radiotherapy treatment planning task using the modified deep learning engine to generate second output data associated with a second particular patient from the second set of patients based on input data associated with the second particular patient.

9. The non-transitory computer-readable storage medium of claim 8, wherein generating the modified deep learning engine comprises:
generating a set of modified weight data associated with multiple processing layers of the modified deep learning engine by modifying weight data associated with multiple processing layers of the deep learning engine.

10. The non-transitory computer-readable storage medium of claim 8, wherein obtaining the deep learning engine comprises:
obtaining the deep learning engine from a central planning system that is configured to train the deep learning engine based on the first training data, wherein the first training data represents global training data, and the second training data represents local training data accessible by the computer system.

11. The non-transitory computer-readable storage medium of claim 8, wherein obtaining the modified output data comprises:
obtaining the modified output data that includes the one or more modifications made by a particular planner according to the second planning rule.

12. The non-transitory computer-readable storage medium of claim 8, wherein performing the radiotherapy treatment planning task comprises one of the following:
performing automatic segmentation to generate output structure data based on input image data associated with the particular patient;
performing dose prediction to generate output dose data based on input image data and input structure data associated with the particular patient; and
performing treatment delivery data prediction to generate treatment delivery data based on input dose data associated with the particular patient.

13. The non-transitory computer-readable storage medium of claim 12, wherein obtaining the modified output data comprises:
obtaining modified output structure data that includes at least one of the following modifications: a modified segmentation margin around a structure; an extension of a structure in a particular direction; a cut of one part of a structure; a modified cutting plane of a structure; and modified margins at different sides of a structure.

14. The non-transitory computer-readable storage medium of claim 12, wherein obtaining the modified output data comprises:
obtaining modified output dose data that includes at least one of the following modifications: modified organ sparing, modified target coverage, modified target dose prescription, and modified normal tissue dose prescription.

15. A computer system configured to perform radiotherapy treatment planning based on continuous deep learning, wherein the computer system comprises: a processor and a non-transitory computer-readable medium having stored thereon instructions that, when executed by the processor, cause the processor to:
obtain a deep learning engine that is trained to perform a radiotherapy treatment planning task based on first training data associated with a first planning rule devised for a first set of patients, wherein the first training data represents data of the first set of patients;
based on input data associated with a first particular patient from a second set of patients, perform the radiotherapy treatment planning task using the deep learning engine to generate first output data associated with the first particular patient;
obtain modified output data that includes one or more modifications to the output data generated by the deep learning engine, wherein the modified output data is generated based on a second planning rule devised for the second set of patients;
based on the modified output data, generate second training data associated with the second planning rule, wherein the second training data includes the modified output data;
generate a modified deep learning engine by re-training the deep learning engine using a combination of the first training data and the second training data, wherein the modified deep learning engine is configured to generate output data for the second set of patients; and
perform the radiotherapy treatment planning task using the modified deep learning engine to generate second output data associated with a second particular patient from the second set of patients based on input data associated with the second particular patient.

16. The computer system of claim 15, wherein the instructions for generating the modified deep learning engine cause the processor to:

generate a set of modified weight data associated with multiple processing layers of the modified deep learning engine by modifying weight data associated with multiple processing layers of the deep learning engine.

17. The computer system of claim 15, wherein the instructions for obtaining the deep learning engine cause the processor to:

obtain the deep learning engine from a central planning system that is configured to train the deep learning engine based on the first training data, wherein the first training data represents global training data, and the second training data represents local training data accessible by the computer system.

18. The computer system of claim 15, wherein the instructions for obtaining the modified output data cause the processor to:

obtain the modified output data that includes the one or more modifications made by a particular planner according to the second planning rule.

19. The computer system of claim 15, wherein the instructions for performing the radiotherapy treatment planning task cause the processor to perform one of the following:

perform automatic segmentation to generate output structure data based on input image data associated with the particular patient;

perform dose prediction to generate output dose data based on input image data and input structure data associated with the particular patient; and perform treatment delivery data prediction to generate treatment delivery data based on input dose data associated with the particular patient.

20. The computer system of claim 19, wherein the instructions for obtaining the modified output data cause the processor to:

obtain modified output structure data that includes at least one of the following modifications: a modified segmentation margin around a structure; an extension of a structure in a particular direction; a cut of one part of a structure; a modified cutting plane of a structure; and modified margins at different sides of a structure.

21. The computer system of claim 19, wherein the instructions for obtaining the modified output data cause the processor to:

obtain modified output dose data that includes at least one of the following modifications: modified organ sparing, modified target coverage, modified target dose prescription, and modified normal tissue dose prescription.

* * * * *